United States Patent
Hobbs et al.

(10) Patent No.: US 6,235,312 B1
(45) Date of Patent: May 22, 2001

(54) LIQUID CRYSTALLINE PHASE DRUG DELIVERY VEHICLE

(75) Inventors: Howard Kenneth Hobbs; Sol Benkendorf; Stephen Hong-Wei Wu, all of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/312,109

(22) Filed: May 14, 1999

(51) Int. Cl.$^7$ .............................. A61K 9/10; A61K 47/14
(52) U.S. Cl. .......................... 424/484; 514/943; 514/944; 516/108; 516/900; 516/29
(58) Field of Search ...................... 514/310, 943, 514/944; 424/484; 516/108, 900, 29; 512/4

(56) References Cited

U.S. PATENT DOCUMENTS 4,346,086  8/1982  Sattler et al. .

FOREIGN PATENT DOCUMENTS 4224507  8/1992  (JP) .
514588   5/1976  (SU) .

OTHER PUBLICATIONS

Larson, K., Cubic Lipid–Water Phases: Structures and Biomembrane Aspects, Journal of Physical Chemistry, vol. 93 (1989), pp. 7304–7314.

Krog et al, Applications in the Food Industry: I, Encyclopedia of Emulsion Technology, vol. 2 (1985) N.Y., Marcel Dekker, Inc., pp. 327–330.

Engstrom, S., Drug Delivery from Cubic and Other Lipid–Water Phases, Lipid Technology, vol. 2, No. 2, (Apr. 1990), pp. 42–45.

*Primary Examiner*—Edward J. Webman
(74) *Attorney, Agent, or Firm*—Michael J. Blake; Harry J. Gwinnell

(57) ABSTRACT

The composition disclosed herein comprises about 55 to about 90 weight percent of a monoglyceride component comprising a monoglyceride having an acyl chain of 12 to 22 carbons, about 5 to about 35 weight percent of an acetylated monoglyceride component comprising an acetylated monoglyceride having an acyl chain of 12 to 22 carbons, and about 2 to about 40 weight percent water. The present composition is a liquid crystalline phase composition at a temperature of about 20 to about 80° C., preferably a cubic liquid crystalline gel.

27 Claims, No Drawings

LIQUID CRYSTALLINE PHASE DRUG DELIVERY VEHICLE

FIELD OF THE INVENTION

The present invention relates to the field of drug delivery systems. Particularly, it relates to liquid crystalline phase drug delivery systems. More particularly, it relates to topical and oral liquid crystalline phase drug delivery systems.

BACKGROUND

Delivery of pharmaceutical agents incorporated in topical drug formulations often proves difficult. Oily materials such as petrolatum are commonly used as the base in topical skin care formulations to prevent moisture loss from skin. However, a number of pharmaceutical agents are difficult to administer topically because they are either incompatible with the oily base material, or else poorly absorbed in the skin. In either case, such incompatible pharmaceutically active drug tends to slowly crystallize and precipitate out of the oil-based or water-based formulation. Such crystallization and precipitation of the active drug results in reduced effectiveness of the drug to the skin. An additional drawback of oil-based topical formulations is that they are often deleteriously greasy for convenient usage.

Delivery of poorly soluble orally administered drugs is lowered due to similar difficulties. The delivery of water insoluble drugs at an absorption site in the gastrointestinal tract is low partly due to insolubility of the drug in the aqueous gastric environment.

Aqueous emulsions employing food grade or pharmaceutical grade polar lipids as emulsifiers have been used as vehicles to deliver both water insoluble drugs and oil-incompatible drugs. For instance, U.S. Pat. No. 4,346,086 discloses a topical cream formulation containing fatty acid sorbitan ester, fatty acid monoglyceride, beeswax, liquid paraffin, petroleum jelly, and water as a delivery vehicle for anti-inflammatory steroids. As a further example, JP 04,224, 507 discloses a transparent gel composition having appropriate fluidity and softness for skin cleansing applications. The composition includes a) one or more hydrophilic surfactants of polyoxyethylene sorbitol fatty acid esters, b) polyoxyethylene glycerol fatty acid esters and one or more lipophilic surfactants of mono-and diesters of diglycerol with branched or unsaturated fatty acids, c) polyhydric alcohol, d) liquid or paste oil ingredient(s), and e) water. These two topical drug delivery vehicles are undesirably complex, both with regards to composition as well as in method of preparation.

SU 514,588 discloses that a mixture of monoglyceride, acetylated monoglyceride, gelling agent, and glycerin displays film-forming properties when present in a very low concentration aqueous solution. Disclosed is a composition of 0.5–5 weight percent gelling agent, 1–3 weight percent acetylated monoglyceride, 0.5–1 weight percent monoglyceride, 1–3 weight percent glycerin, with the balance being water. A thin coating of this liquid composition forms a solid film on fruit under ventilation.

An alternative type of drug delivery system is a binary composition formed from a monoglyceride lipid and water. It is known that such binary monoglyceride-water systems form liquid crystalline gel phases in the useful drug delivery temperature range of about 20 to about 40° C. Liquid crystalline phases are commonly divided into the three main categories of lamellar, hexagonal, and cubic phases. All three liquid crystalline phases may be formed in a monoglyceride-water binary system in the temperature range of about 20 to about 40° C.

Binary monoglyceride-water liquid crystalline phase compositions have been researched for use as sustained-release drug carriers. For example, see Larson, K. *Cubic Lipid-Water Phases: Structures and Biomembrane Aspects.* Journal of Physical Chemistry, Vol 93 (1989), pp. 7304–7314. Liquid crystalline systems act as sustained release drug emulsifiers due to the physical liquid crystalline structure. Specifically, a binary lamellar phase system exists as a one-dimensional sandwich-type structure having alternating layers of lipid and water. A binary hexagonal phase is periodic in two dimensions. A binary cubic phase liquid crystalline system is a periodic curved bilayer extending in three dimensions, separating two congruent networks of water channels. A fully swelled cubic phase (having about 50 weight percent water) is highly viscous and has a water pore diameter for receiving active agents of up to about 5 nm. When formed from food- or pharmaceutical-grade monoglycerides, these physical properties make binary liquid crystalline phase compositions in situ-forming biodegradable matrix systems. The particular liquid crystalline phase(s) formed by a binary monoglyceride-water composition is dependent upon the ratio of monoglyceride to water, and temperature. Liquid crystalline phase diagrams of binary compositions of 1-monoglycerides in water are illustrated by Krog, Riisom, and Larsson, in "*Applications in the Food Industry: I*", Encyclopedia of Emulsion Technology, Vol. 2. (1985) N.Y., Marcel Dekker, Inc., pp. 327–329, incorporated herein by reference.

The drug delivery effectiveness of a binary monoglyceride-water liquid crystalline phase composition is partly determined by the weight ratio of monoglyceride to water. Binary liquid crystalline phase systems are categorized as having either a relatively high or low water content. A "high water content" binary monoglyceride-water composition having a weight ratio of from about 1:1 to about 4:1 monoglyceride to water is well suited for delivering either water-soluble or lipid-soluble drugs. A "low water content" binary monoglyceride-water composition having a weight ratio greater than about 4:1 monoglyceride to water is well suited for delivering water-insoluble drugs. A useful liquid crystalline phase drug delivery composition should be homogeneous. A binary composition having a weight ratio less than about 1:1 monoglyceride to water is not useful because it deleteriously separates into aqueous and liquid crystalline phases.

Engstrom found that the highly ordered structure of binary monoglyceride-water cubic phase compositions makes cubic liquid crystalline phase compositions very useful in drug delivery, due to the fact that they have very prominent lipid and water domains, which may solubilize both water- and lipid-soluble substances, as well as molecules with pronounced amphiphilic characters. Engstrom, S. *Drug Delivery from Cubic and other Lipid-Water Phases,* Lipid Technology, Vol. 2, no. 2 (April 1990), pp. 42–45. However, the high viscosity (greater than 2 M cPs) and stiffness of a binary monoglyceride-water cubic phase having a high water content is deleteriously limiting for topical and oral gel delivery applications. Such high viscosity compositions are difficult to process, as well as being difficult to extend and spread during topical application. For that reason, Engstrom's research was directed towards developing methods for forming aqueous dispersions of the binary monoglyceride-water cubic phase for oral delivery.

Within the pertinent drug delivery temperature range of about 20 to about 40° C., the viscosity of a binary monoglyceride-water liquid crystalline system having relatively low water content (ratio of at least 4:1 weight of monoglyceride to water) is too low for use as a topical gel. The desired viscosity for a topical formulation is from about 20 to about 12,000 cPs. Gel formation occurs at a viscosity of about 500 cPs. Gel formation is an important property for drug delivery vehicles used to topically or orally deliver many difficult-to-deliver drugs. Gel formation of the vehicle helps prevent crystallization and precipitation of the water-insoluble and lipid-incompatible drugs that would benefit the most from delivery by an emulsion-type vehicle.

In light of the above, it would be desirable to provide a liquid crystalline phase drug delivery vehicle for both topical and oral drug delivery having a viscosity high enough to form a gel, yet low enough to be easily processable and extendable, in the temperature range of about 20 to about 40° C. It would be further desirable for such liquid crystalline composition to include both high and low water content formulations for usefulness in the delivery of drugs having a broad solubility range. It would be even further desirable for such composition to be relatively simple, both with regards to composition as well as in method of preparation.

SUMMARY OF THE INVENTION

The composition of the present invention comprises about 55 to about 90 weight percent of a monoglyceride component having a monoglyceride with an acyl chain of 12 to 22 carbons, about 5 to about 35 weight percent of an acetylated monoglyceride component having an acetylated monoglyceride with an acyl chain of 12 to 22 carbons, and about 2 to about 40 weight percent water. The weight percentages used herein are based on the total weight of these three components.

DETAILED DESCRIPTION

The composition of the present invention has unexpectedly beneficial characteristics making it useful as a gel vehicle for topical and oral delivery of drugs. The composition of the present invention exists in a liquid crystalline phase having a viscosity high enough for gel formation, yet low enough for processability and extendibility under normal drug storage and delivery temperatures. The composition of the present invention has about 55 to about 90 weight percent and preferably from about 65 to about 85 weight percent, of a monoglyceride having a $C_{12}$ to $C_{22}$ fatty acid acyl chain, about 5 to about 35 weight percent and preferably from about 10 to about 30 weight percent of an acetylated monoglyceride having a $C_{12}$ to $C_{22}$ fatty acid acyl chain, and about 2 to about 40 weight percent and preferably from about 5 to about 25 weight percent water, wherein the total of the weight percentages of these three components equals 100 weight percent.

It was surprisingly found that the presence of acetylated monoglyceride, in combination with monoglyceride and water, serves as a type of viscosity buffer in that the acetylated monoglyceride lowers the viscosity of the high water content monoglyceride-water systems (a weight ratio of about 1:1 to about 4:1 monoglyceride to water), yet raises the viscosity of low water content monoglyceride-water systems (a weight ratio of more than about 4:1 monoglyceride to water). Advantageously, the viscosity of both the high and low water content formulations of the composition of the present invention is within the range of viscosities useful for topical and oral gel applications. For example, when the present composition has a weight ratio of about 1:1 to about 4:1 monoglyceride to water (high water content), the viscosity is preferably at least about ten times lower than the viscosity would be in the absence of acetylated monoglyceride. When the present composition has a weight ratio of greater than about 4:1 monoglyceride to water (low water content), the viscosity is preferably about ten times higher than the viscosity would be in the absence of acetylated monoglyceride.

An additional benefit of the present invention is that the temperature at which the composition attains the gelling viscosity of at least about 500 cPs, the "gel temperature", is also improved when compared to a binary monoglyceride-water system having a similar weight ratio of monoglyceride to water. Low water content formulations of the present composition gel at a temperature of about 5 to 15° C. higher than the gel temperature of a binary monoglyceride-water system. High water content formulations of the present composition gel at a temperature at least about 10° C. lower than the gel temperature of a similar binary monoglyceride-water system. This gel temperature buffering effect improves the processability of various formulations of the composition under typical processing temperatures. The relative increase in gel temperature of low water content formulations is beneficial since a topical formulation of the present composition is an extendable liquid that adheres to skin in the typical usage temperature range, instead of deleteriously dripping off skin as would a low water content binary monoglyceride-water formulation.

It should be understood that reference herein simply to "monoglyceride", versus "acetylated monoglyceride", specifically refers to non-acetylated monoglycerides. The term "liquid crystalline phase" as used herein is used to denote an intermediate state between solid crystals and isotropic liquids, characterized by long-range order and short-range properties close to those of a simple liquid or solution. The liquid crystalline phase can be in the form of a lamellar phase, a hexagonal phase, a reverse hexagonal phase, a cubic phase, or a combination thereof. The present composition preferably exists as a cubic liquid crystalline gel.

The composition of the present invention has a viscosity between about 10 to about 25,000 cPs in the temperature range between about 20 to about 80° C. In the storage and application temperature range of about 20 to about 40° C., the viscosity is preferably between about 20 to about 20,000 cPs, with a viscosity between about 100 to about 15,000 cPs being more preferable. The composition of the present invention remains in a single liquid crystalline phase at a temperature of about 20 to about 80° C. The composition begins to solidify at lower temperatures. At higher temperatures, the composition tends to lose moisture content, thereby changing the gelling and drug delivery characteristics of the composition.

The monoglycerides of the present composition may be produced by the interesterification reaction of triglycerides containing $C_{12}$ to $C_{22}$ acyl chains with glycerol. This interesterification reaction produces a mixture of mono-, di-, and tri-glycerides. The monoglyceride component is preferably substantially comprised of a monoglyceride. A high monoglyceride content is attainable through distillation of the interesterification reaction glyceride mixture. The monoglyceride component is preferably formed from a distilled monoglyceride having at least 90 weight percent monoester content.

The monoglyceride of the present invention is preferably a 1-monoglyceride. The monoglyceride component is preferably formed from monoglyceride having at least 65 weight percent 1-monoglyceride content. A high percentage of 1-monoglyceride, with low 2-monoglyceride content, is also attained through distillation of the interesterification reaction glyceride mixture.

Monoglycerides having a saturated fatty acid acyl chain and those having an unsaturated fatty acid acyl chain are useful in the present composition. Preferably, the dominant monoglyceride used includes an unsaturated fatty acid acyl chain because saturated monoglycerides form cubic phase systems only at high temperatures (about 70 to 100° C.), whereas unsaturated monoglycerides provide cubic phase formation at body temperature. The monoglyceride preferably has an HLB from about 2 to 6, preferably from about 3.5 to 4.5, and a melting temperature of about 30 to about 45° C. Examples of suitable $C_{12}$ to $C_{22}$ fatty acid acyl chain groups include the esters of palmitic ($C_{16}$:0), stearic ($C_{18}$:0), oleic ($C_{18}$:1), linoleic ($C_{18}$:2), linolenic ($C_{18}$:3), gadoleic ($C_{20}$:1) and behenic ($C_{22}$:0) acids, and combinations thereof. The parenthetical designation for each of the acids listed above indicates the number of carbon atoms in the chain and the number of unsaturated bonds in the fatty acid ester chain. The $C_{12}$ to $C_{22}$ monoglycerides are capable of forming a liquid crystalline phase or a mixture of different liquid crystalline phases when mixed with water, depending upon the water content and the temperature. The preferred monoglycerides are include glyceryl monooleate (oleic acid acyl chain) and glyceryl monolinoleate (linoleic acid acyl chain). These monoglycerides are preferred because they predominantly form the desirable cubic liquid crystalline phase in water. The molecular formula of glyceryl monooleate is shown below as formula I. The molecular formula of glyceryl monolinoleate is shown below as formula II.

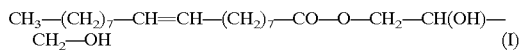

$$CH_3-(CH_2)_7-CH=CH-(CH_2)_7-CO-O-CH_2-CH(OH)-CH_2-OH \quad (I)$$

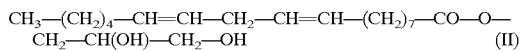

$$CH_3-(CH_2)_4-CH=CH-CH_2-CH=CH-(CH_2)_7-CO-O-CH_2-CH(OH)-CH_2-OH \quad (II)$$

The acetylated monoglyceride includes an acyl chain having 12 to 22 carbons. The acyl chains suitable for the acetylated monoglyceride are the same acyl chain groups listed above with regards to the monoglyceride. A combination of different acetylated monoglycerides can be used in the present composition.

The acetylated monoglyceride is preferably a distilled acetylated monoglyceride having at least 90 weight percent 1-monoglyceride ester content, with the degree of acetylation at the number 2 and 3 carbons being greater than 96 weight percent. The acetylated monoglyceride preferably has an HLB value from about 2 to 6, more preferably from about 3.5 to about 4.5, a melting temperature between about 4 to about 12° C., and a saponification value of about 370 to 382.

The monoglycerides of the present composition may be produced by the interesterification reaction of triglycerides containing $C_{12}$ to $C_{22}$ acyl chains with glycerol, preferably followed by distillation. The acetylated monoglycerides may be produced by the interesterification reaction of triglycerides containing $C_{12}$ to $C_{22}$ acyl chains with glyceryl triacetate (triacetin), preferably followed by distillation. The fatty acid portion of the triglyceride becomes the acyl chain of the monoglyceride. Examples of sources of triglycerides used for producing the monoglyceride and acetylated monoglyceride of the present composition include hydrogenated palm oil, hydrogenated soybean oil, hydrogenated cottonseed oil, refined palm oil, hydrogenated soybean oil, refined sunflower oil, refined cottonseed oil, hydrogenated coconut oil, and refined canola oil. These oils have a mixture of fatty acid acyl chain lengths. The fatty acid distribution of monoglyceride produced from such oils will be the same as the fatty acid distribution of its parent oil. Therefore, the monoglyceride and acetylated monoglyceride components of the present composition will most likely be a mixture of monoglycerides and acetylated monoglycerides having a variety of acyl chain lengths. Accordingly, the composition is disclosed herein as having a "monoglyceride component" instead of a single monoglyceride moiety. The presence of a small amount (less than 5%) of monoglycerides having an acyl chain length other than 12 to 22 carbons in the monoglyceride component has no substantial effect on the composition. The fatty acid distribution of the glyceryl monolinoleate, the glyceryl monooleate, and the acetylated monoglyceride used in the Examples is shown in Table 3 in the Examples section below.

The composition of the present invention may further include an active agent dispersed throughout the liquid crystalline phase, in either the water domain or the lipid domain. Useful active agents include hydrophobic compounds, hydrophilic compounds, and amphiphilic compounds, particularly pharmaceutical agents. Examples of useful pharmaceutical agents to be delivered by way of the composition of the present invention includes vitamins, proteins and peptides, nucleic acids, growth promoter for wound treatment, particularly oil soluble materials and poorly water-soluble drugs. Other useful active ingredients include fragrances, sunscreens, antifungals, antibiotics, benzocaine (ethyl-amino benzoate), phenols, polymers, insect repellents, preservatives, steroids, antimicrobials, emollients, humectants, moisturizers, astringents, deodorants, as well as other compatible materials which may be desired to enhance the cosmetic and pharmaceutical properties of the composition. The concentration of the active agent would vary widely depending upon the particular agent selected and the results desired.

The composition of the present invention may be made by mixing the monoglyceride, acetylated monoglyceride and water together in a vessel at about 60 to 90° C., preferably at a temperature of about 65 to 80° C. More particularly, monoglycerides, acetylated monoglycerides, oily substances or active ingredients are mixed together in molten lipid phase, and then water is added slowly to the desirable ratio. It is preferable to introduce the active ingredient prior to or during formation of the liquid crystalline phase. An active agent such as a drug may be incorporated into the liquid crystalline composition by first introducing it to the molten lipid phase, or by mixing it in the aqueous phase, then adding to the molten lipid phase.

Additives not negatively effecting the properties of the liquid phase gel composition of the present invention may also be incorporated into the composition. Examples of suitable additives include waxes, such as, canauba wax and beeswax, and thickneners. Such additives are preferably added at a concentration less than about 10 percent of the total weight of the composition.

The composition of the present invention may be applied to skin, mucosal membranes, and tissues for delivery of bioactive ingredients. When the composition is applied to the skin, it provides a thin, substantive, yet flexible film that does not crack, peel or flake. The composition has a slippery feel on the skin and a good adhesive property on skin or mucosal tissues. The composition will absorb water from outside sources and hold water on the skin or tissue surface. It is possible that even after several washings, the skin will still have a thin layer of the gel composition. The time release of the active agent would depend on the active agent and the liquid crystalline matrix structure.

In another embodiment of the invention, the composition of the present invention is a low water content (weight ratio greater than 4:1 monoglyceride to water) liquid formulation for mixing with a sufficient amount of water to raise the gel temperature to the application temperature, thereby forming a gel. The additional water mixed with the low water content composition may come from a variety of sources. For instance, a low water content liquid composition would be useful as a shaving liquid that would gel upon mixing with tap water, or a liquid mouthwash that would gel to coat the mouth or throat upon mixing with saliva.

A low water content composition of the present invention can also be beneficially used to take advantage of both extrinsic water sources and extrinsic heat. The present invention further includes a method of providing a low water content gel formulation of the present composition at a temperature below it's gel temperature. The gel formulation is then contacted with water, such as a moist treatment site, having a temperature higher than the gel temperature for a period of time sufficient to allow the temperature of the composition to rise above the gel temperature, thereby forming a liquid. At some point during this transformation, the excess moisture available from the moist treatment site is absorbed into the formulation, thereby increasing the water content of the formulation. The gel temperature of the low water content composition will increase upon absorption of a sufficient amount of water, thereby promoting a re-transformation into a gel phase. This type of application is very beneficial for topical drug delivery to skin, and may have such use applications as a burn cream or antiseptic. In instances when it is not desirable to absorb moisture from the treatment site, such as a burned skin, the treatment method may include separately moistening the low water content formulation with another source of water.

A preferred embodiment of such method is the application of a gel form of a tertiary composition of the present composition having a gel temperature less than about 0° C. and having a weight ratio of greater than about 20:1 of monoglyceride to water (less than 5 weight percent water content) to moist skin, mucosal membrane, or tissue having a temperature of at least about 30° C. After rubbing the gel across the skin for a short period of time, the temperature of the composition rises above the gel temperature, and the gel transforms to a liquid. Then, with further rubbing, the liquid composition easily absorbs enough moisture from the skin and/or the environment to raise the water content in the composition to about 10 weight percent. Since the higher water content composition formed will exhibit an increased gel temperature, the composition transforms to a stiff gel adhering well to the skin's surface to provide a good barrier and a good time released drug delivery vehicle.

The composition of the present invention is also beneficial for use in forming sustained release gel capsules for oral drug delivery. The improved processability of the composition is beneficial.

EXAMPLES

The examples below are intended to illustrate, but not limit, the scope of the present invention. All parts and percentages in the examples are on a weight basis unless otherwise stated.

The monoglycerides used in the following examples were predominantly glyceryl monooleate ("monoolein") and glyceryl monolinoleate ("monolinolein") available commercially from Eastman Chemical Company as EASTMAN 18-99 MONOOLEIN DISTILLED MONOGLYCERIDE, and EASTMAN 18-92 MONOLINOLEIN DISTILLED MONOGLYCERIDE. The monoolein was commercially prepared by the reaction of partially hydrogenated canola oil with glycerol. The monolinolein was commercially prepared by the reaction of sunflower oil with glycerol. Both distilled monoglycerides are semiplastic waxy solids. The properties of these two commercial monoglycerides are given in Table 1.

TABLE 1

|  | monoolein | monolinolein |
|---|---|---|
| Monoester content, minimum | 90% | 90% |
| Glycerol content, maximum | 1.2% | 1.2% |
| Acid value, max. | 3 | 3 |
| HLB value | 3.8–4.0 | 3.8–4.0 |
| Iodine value | 90–95 | 105–115 |
| Specific gravity | 0.93 | 0.90 |
| Melting temperature | 35° C. | 41° C. |

The acetylated monoglyceride used in the following examples is predominantly acetylated glyceryl linoleate and is commercially available from Eastman Chemical Company as EASTMAN 9-45 ACETYLATED MONOGLYCERIDE, with the typical properties are shown below in Table 2.

TABLE 2

| Acetylated Monoglyceride | |
|---|---|
| Acetylation, minimum % | 96% |
| Melting Temperature | 4–12° C. |
| Specific Gravity | 0.94 |
| HLB Value | 3.8–4.0 |
| Hydroxyl Value | 0–15 |
| Saponification Value | 370–382 |
| Glycerol content, maximum % | 1.5% |
| Iodine Value | 43–53 |
| Acid Value, maximum | 3 |

The fatty acid distribution of the two monoglycerides used, monoolein and monolinolein, and the acetylated monoglyceride used is shown in Table 3. The fatty acid acyl chain is described below in terms of the chain length and the number of unsaturated carbon bonds in the acyl chain. The data for the acetylated monoglyceride excludes residual acetic acid.

TABLE 3

| Acyl Chain Fatty Acid | Monolinolein | Monoolein | Acetylated Monoglyceride |
|---|---|---|---|
| $C_{12}$ | 0 | 0 | 0 |
| $C_{14}$ | 0.1 | 0.1 | 0.1 |
| $C_{16}$ | 6.6 | 4.6 | 10.8 |
| $C_{18}$ | 4.6 | 1.9 | 12.6 |
| $C_{18}-1$ | 22 | 57 | 73.9 |
| $C_{18}-2$ | 64.1 | 23.3 | 1.9 |
| $C_{20}$ | 0.3 | 0.5 | 0.3 |
| $C_{22}$ | 0.7 | 0.3 | 0.3 |

Example 1 (Comparative)

The purpose of the present example is to illustrate the compatibility of monoglyceride with acetylated monoglyceride, without the presence of water.

A mixture of monolinolein and acetylated monoglyceride having a ratio of 5.7:1 weight of monolinolein to acetylated monoglyceride was melted and blended together at 90° C. Also, a mixture of monolinolein and acetylated monoglyceride having a ratio of 1:1 weight of monolinolein to acetylated monoglyceride was melted and blended together at 90° C. The mixtures formed clear solutions. The viscosity values of the mixtures were measured as the mixtures were cooled to room temperature. The mixtures solidified to form soft waxy solid masses. Similarly, two mixtures having ratios of 5.7:1 and 1:1 weight of monoolein to acetylated monoglyceride were mixed and incubated in a heated oven at 90° C. The mixtures became clear solutions. Upon cooling to room temperature, the mixtures remained as clear solutions. The viscosity data follows in Table 4.

TABLE 4

| Temp. ° C. | monolinolein/ Acet mono 50/50 Visc, (cPs) | monolinolein/ Acet mono 85/15 Visc, (cPs) | monoolein/ Acet mono 50/50 Visc, (cPs) | monoolein/ Acet mono 85/15 Visc, (cPs) |
|---|---|---|---|---|
| 80 | 12 | 12 | 12 | 24 |
| 70 | 18 | 18 | 12 | 30 |
| 60 | 24 | 30 | 18 | 36 |
| 50 | 30 | 42 | 30 | 66 |
| 40 | 42 | 78 | 42 | 120 |
| 30 | 66 | 132 | 84 | 174 |
| 20 | 400 (Solid) | 1700 (Solid) | 126 (Liquid) | 258 (Liquid) |

Viscosity data were measured using a Brookfield viscometer, Model LVDV-I. A number 4 spindle was used. The rotation speed was 100 rpm. The viscosity unit is given in centi-poise per second (cPs). The four binary mixtures formed homogenous phases, indicating that the monoglycerides and acetylated monoglyceride are compatible.

Example 2 (Comparative)

This example shows that although acetylated monoglyceride is compatible with glyceryl triacetate, no gel was formed when water was added to a mixture of acetylated monoglyceride and glyceryl-triacetate.

Acetylated monoglyceride and glyceryl triacetate ("TRIACETIN" available from Eastman Chemical Company), were mixed at the ratios as shown in Table 5. A clear liquid was formed at all ratios. When an amount of water, equivalent to 10% by weight of the mixture was added, the solution became cloudy and no gel formation was observed. When compared to Examples 4–8, this example shows that the effect of water added to a compatible binary acetylated monoglyceride mixture is unexpectedly different when the compatible binary mixture is formed of acetylated monoglyceride and monoglyceride.

TABLE 5

Compatibility of Acet. Monoglyceride and Glyceryl Triacetate

| Acet. Mono: Triacetate | Density | Viscosity, cPs |
|---|---|---|
| 1:0 | 0.94 | 48 |
| 2:1 | 1.01 | 38 |
| 1:1 | 1.05 | 36 |
| 1:2 | 1.09 | 32 |
| 0:1 | 1.16 | 28 |

It should be pointed out that since a 1:1 ratio of acetylated monoglyceride to glyceryl triacetate, the mixture has a density close to 1.0, the binary composition would be particularly useful for injection applications.

Example 3 (Comparative)

This example shows the phase properties and viscosity of binary mixtures of monolinolein or monoolein and water (with no acetylated monoglyceride) at a temperature range from 25 to 60° C. A 50 gram sample of monoglyceride was melted. Distilled water was slowly added to the molten monoglyceride. When a ratio of 5.7:1 weight monoglyceride to water was attained, the viscosity values of the binary system was measured as follows in Table 6:

TABLE 6

| Temp, ° C. | Viscosity, cPs 5.7:1 monolinolein-water | Viscosity, cPs 5.7:1 monoolein-water |
|---|---|---|
| 60 | 75 | 72 |
| 55 | 93 | 90 |
| 50 | 120 | 120 |
| 45 | 192 | 160 |
| 40 | 270 | 1000 |
| 35 | 550 | 1500 |
| 30 | 1000 | 1530 |

It can be seen by comparison that a binary mixture of monoglyceride and water exhibits much higher viscosity data than the respective data given in Example 1 where acetylated monoglyceride was mixed with monoglyceride. These results indicate gel formation when water is mixed with monoglycerides. The gel temperature is defined as the temperature at which liquid medium viscosity is greater than 500 cPs. For monolinolein-water (5.7:1) and monoolein-water (5.7:1), the gel formation temperatures were determined to be approximately 35° C. and 42° C., respectively.

When the monolinolein-water and monoolein-water ratios were adjusted to reach a ratio of 2.3:1 (70:30) weight percent monoglyceride to water, both mixtures formed a hard gel with a viscosity much greater than 2 M cPs at 60° C. The gels were extremely difficult to process. When the ratios were adjusted to 1:1, the mixtures no longer formed homogeneous gel blends. Liquid was observed on the gel. When these mixtures were placed in a 90° C. oven, the gel solid did not melt to form a liquid phase, indicating a gel formation temperature greater than 90° C.

These data confirm that a binary mixture of monoolein or monolinolein with water forms liquid crystalline phases. The cubic phase of this binary system is so extremely viscous that its applications are limited.

Example 4

A gel composition of the present invention was prepared by the following method.

Step 1: Heated monolinolein and acetylated monoglyceride to form a molten mixture, and adjusted the weights of monolinolein to acetylated monoglyceride to the desired weight ratios.
Step 2: Water was added to the molten mixture formed in Step 1.
Step 3: Cooled the mixture formed in Step 2, while continually mixing, to form a clear gel.

The phase behaviors and viscosity data of the gel compositions comprising a ratio of 5.7:1 weight of monolinolein to acetylated monoglyceride at various water concentrations are given in Table 7. (monolinolein=Monolin, acetylated monoglyceride=A-mono).

TABLE 7

Ratio of 5.7:1 Monolinolein to Acetylated Monoglyceride

| (Wgt %) Monolin | /A-mono | /Water | Appearance at 25° C. | Viscosity, cPs |
|---|---|---|---|---|
| 85.0 | /15.0 | /0.0 | solution with precipitate | 5.7 |
| 80.8 | /14.2 | /5.0 | clear solution | 1.6 |
| 76.5 | /13.5 | /10.0 | clear gel | 23,862 |
| 68.0 | /12.0 | /20.0 | clear gel | 31,005 |
| 59.5 | /10.5 | /30.0 | phase separated | 193,420 |
| 61.0 | /9.0 | /40.0 | phase separated | 69,694 |
| 46.8 | /8.2 | /45.0 | phase separated | 48,985 |

The viscosity was measured at 25° C. using a parallel plate method, 40 mm in length and 1 mm in gap, and a frequency sweep at 0–100 rad/sec.

Example 5

This example shows the phase behaviors of a monolinolein-acetylated monoglyceride-water composition at room temperature.

A series of ternary blends were prepared by adding water to a binary blend having a ratio of 5.7:1 weight of monolinolein to acetylated monoglyceride according to the method described in Example 4. The appearances of the mixtures after 48 hours are shown in Table 8 (monolinolein=Monolin, acetylated monoglyceride=A-mono).

TABLE 8

Ratio of 5.7:1 Monolinolein to Acetylated Monoglyceride

| (wt %) Monolin | /A-mono | /Water | Appearance at 25° C. After 48 hrs. |
|---|---|---|---|
| 85.0 | /15.0 | /0.0 | Crystals found in liquid. |
| 80.8 | /14.2 | /5.0 | Clear liquid |
| 6.5 | /13.5 | /10.0 | Clear gel |
| 72.3 | /12.8 | /15.0 | Clear gel |
| 68.0 | /12.0 | /20.0 | Clear gel |
| 63.8 | /11.2 | /25.0 | Clear gel (viscosity = 320,000 cPs) |
| 59.5 | /10.5 | /30.0 | Clear gel, phase separated |
| 51.0 | /9.0 | /40.0 | Clear gel, phase separated |
| 46.8 | /8.2 | /45.0 | Clear gel, phase separated |
| 42.5 | /7.5 | /50.0 | Clear gel, phase separated |
| 34.0 | /6.0 | /60.0 | white dispersion, phase separated |
| 25.5 | /4.5 | /70.0 | white dispersion, phase separated |
| 21.2 | /3.8 | /75.0 | white dispersion, phase separated |
| 17.0 | /3.0 | /80.0 | white dispersion, phase separated |
| 8.5 | /1.5 | /90.0 | phase separated |

Example 6

This example illustrates the phase and viscosity behaviors of ternary monolinolein-acetylated monoglyceride-water and monoolein-acetylated monoglyceride-water mixtures at different temperatures. Gel temperature or melting temperature was defined as the temperature at which the gel structure begins to solidify or melt and exhibits a viscosity value of greater than 500 cPs.

TABLE 9

| Wt. % Monolin | /A-mono | /Water | Appearance at 70° C. and 90° C. | Gel Temp. | Appearance at Rm Temp |
|---|---|---|---|---|---|
| 80.8 | /14.2 | /5.0 | Clear liquid | ==== | Clear liq. |
| 74.0 | /13.0 | /13.0 | Clear liquid | 46° C. | Clear gel |
| 62.1 | /11.0 | /27.0 | Two liq layers | ---- | Soft gel + liq. |
| 45.1 | /8.0 | /47.0 | Two liq layers | ---- | Soft gel + liq. |
| 85 | /0 | /15 | Clear liquid | 35° C. | Gel |
| 70 | /0 | /30 | Viscous gel + liq | ---- | Hard gel + liq. |
| 50 | /0 | /50 | Viscous gel + liq | ---- | Hard gel + liq. |

The symbol === indicates that the gel temp was not measured, and ---- indicates that the gel temperature was not measurable.

TABLE 10

| wt % Monoolein | /A-mono | /Water | Appearance at 70° C. and 90° C. | Gel Melting Temperature | Appearance at Rm. Temp |
|---|---|---|---|---|---|
| 80.8 | /14.2 | /5.0 | Clear liquid | ==== | Clear liq. |
| 74.0 | /13.0 | /13.0 | Clear liquid | 46° C. | Clear gel |
| 62.1 | /11.0 | /27.0 | Two liquid layers | ---- | Soft gel + liq. |
| 45.1 | /8.0 | /47.0 | Two liquid layers | ---- | Soft gel + liq. |
| 85 | /0 | /15 | Clear liquid | 35° C. | Gel |
| 70 | /0 | /30 | Viscous gel + liq | ---- | Hard gel + liq. |
| 50 | /0 | /50 | Viscous gel + liq | ---- | Hard gel + liq. |

The symbol === indicates that the gel temp was not measured, and ---- indicates that the gel temperature was not measurable.

The data above shows that the presence of acetylated monoglyceride increased the gel temperature of the composition in the compositions having low water content. In Table 9, the 74.0/13.0/13.0 weight percent tertiary composition and the 85/0/15 weight percent binary monoglyceride-water composition each have a ratio of 5.7:1 weight of monolinolein to water. In Table 10, the 74.0/13.0/13.0 weight percent tertiary composition and the 85/0/15 weight percent binary monoglyceride-water composition each have a ratio of 5.7:1 weight of monoolein to water. Comparison of these low water compositions shows that the presence of acetylated monoglyceride in a low water content composition of the present invention raises the gel temperature, indicating that the viscosity is correspondingly raised at any given temperature within the useful temperature range.

Comparing to Example 3, this example shows that the presence of acetylated monoglyceride increases the gel temperature of the composition. It is also observed that the presence of acetylated monoglyceride made the gel softer when the water content approached 30% before the gel separated.

Example 7

This example further illustrates the effect of acetylated monoglyceride on viscosity properties and gel temperatures for monolinolein-acetylated monoglyceride-water and monoolein-acetylated monoglyceride-water ternary systems having a weight percentage of 62.1% monoglyceride, 11.0% acetylated monoglyceride, and 27.0% water. The data shown below in Table 11 should be compared to a binary (no acetylated monoglyceride) mixture having a ratio of 2.3:1 weight of monolinolein to water and a binary mixture having a ratio of 2.3:1 weight of monoolein to water, which appeared as hard gels with viscosity values much higher than 2 M cPs. This shows the viscosity lowering effect of acetylated monoglyceride in high water content compositions of the present inventions.

TABLE 11

| (wgt %) Monolin 62.1 | /A-mono /11.0 | /Water /27.0 | (wgt %) Monoolein 62.1 | /A-mono /11.0 | /Water /27.0 |
|---|---|---|---|---|---|
| Temp | Viscosity | | Temp | Viscosity | |
| 75° C. | 42 cPs | | 75° C. | 54 cPs | |
| 70 | 42 | | 70 | 78 | |
| 65 | 58 | | 65 | 400 | |
| 60 | 90 | | 62 | 590 | |
| 56 | 240 | | 60 | 1200 | |
| 54 | 350 | | 58 | 4700 | |
| 52 | 1380 | | 57 | >2 M | |
| 50 | 3700 | | | | |

Although phase separations were observed in these two systems, viscosity values of the gel phases at 90° C. were measurable within the instrument limit. The gel formation temperatures were determined to be 52° C. for the 62.1% monolinolein/11.0% acetylated monoglyceride/27.0% water composition and 62° C. for the 62.1% monoolein/11.0% acetylated monoglyceride/27.0% water composition. This was a stark improvement over the viscosity of the comparable binary monoglyceride-water compositions of the same monoglyceride to water ratio (2.3:1). This shows the viscosity lowering effect of acetylated monoglyceride in high water content compositions of the present inventions.

Example 8

This example further illustrates the effect of acetylated monoglyceride in ternary compositions having a weight percentages of 45.1% monolinolein/8.0% acetylated monoglyceride/47.0% water and 45.1% monoolein/8.0% acetylated monoglyceride/47.0% water. These ternary compositions should be compared to a binary monoglyceride-water mixture having a weight ratio of 1:1 monoglyceride to water.

With the presence of acetylated monoglyceride, both gel phases were liquefied at 90° C. But for the monolinolein-water and monoolein-water binary systems at a 1:1 ratio, the gel phases remained as a hard gel even at 90° C. This shows the viscosity lowering effect of acetylated monoglyceride in high water content compositions of the present inventions.

Example 9

This example illustrates a clear gel formulation of the present composition containing an active ingredient, vitamin E.

Step 1: Heated monolinolein, acetylated monoglyceride and vitamin E to form a molten mixture.
Step 2: Added water to the molten mixture formed in Step 1.
Step 3: Cooled the mixture formed in Step 2, while continually mixing.

A clear gel preparation was obtained. The gel composition consisted of:

| | |
|---|---|
| monolinolein | 73.65% |
| acetylated monoglyceride | 8.00% |
| Vitamin E | 5.00% |
| Water | 13.35% |

Example 10

This example illustrates the incorporation of beeswax into the gel vehicle described in Examples 2 and 3. Beeswax was added in Step 1, as shown in Example 2.

| | |
|---|---|
| monolinolein | 56.95% |
| acetylated monoglyceride | 10.05% |
| Beeswax | 3.00% |
| Water | 30.00% |

Example 11

This example shows that Carnauba wax can be incorporated into the gel formulation as given in Example 5.

| | |
|---|---|
| monolinolein | 56.95% |
| acetylated monoglyceride | 10.05% |
| Carnauba wax | 3.00% |
| Water | 30.00% |

Example 12

A combination of beeswax and Carnauba wax was incorporated into the composition shown in Example 5 to provide the following:

| | |
|---|---|
| monolinolein | 53.55% |
| acetylated monoglyceride | 9.45% |
| Carnauba wax | 5.00% |
| Beeswax | 2.00% |
| Water | 30.00% |

Example 13

This example shows that the gel structure can still be maintained upon increasing the concentration of wax.

| | |
|---|---|
| monolinolein | 51.85% |
| acetylated monoglyceride | 9.15% |
| Carnauba wax | 7.00% |
| Beeswax | 2.00% |
| Water | 30.00% |

Example 14

This example illustrates a clear liquid gel composition containing benzocaine and phenol as the active ingredients in the formulation. Benzocaine and phenol were incorporated into an aqueous solution as described in Example 4. The composition is shown as follows.

| | |
|---|---|
| monolinolein | 68.72% |
| acetylated monoglyceride | 12.13% |
| Benzocaine | 5.00% |
| Phenol | .80% |
| Water | 13.35% |

Example 15

This example illustrates a clear gel formulation containing UV-absorber and a preservative.

| | |
|---|---|
| monolinolein | 55.00% |
| acetylated monoglyceride | 2.25% |
| Escalol 557 (SPF of 7) | 7.50% |
| Water | 35.00% |
| Potassium Sorbate | 0.25% |

Example 16

This example illustrates a formulation containing a mixture of UV-absorbers, and a preservative.

| | |
|---|---|
| monolinolein | 55.00% |
| acetylated monoglyceride | 2.25% |
| Escalol 557 (SPF of 7) | 7.50% |
| Escalol 567 | 3.00% |
| Potassium Sorbate | .60% |
| Water | 31.65% |

Example 17

This example illustrates that an aqueous solution containing 35% water-dispersible polymer can be incorporated into the gel formulation. The polymer used is EASTMAN AQ 48, available from Eastman Chemical Company. It is an amorphous polyester that disperses directly in water. This water-dispersible polymer is composed of aromatic dicarboxylic acid unit sand aliphatic or cycloaliphatic glycol units. Some of the aromatic dicarboxylic acid units have sodio-sulfo ($SO_3^-Na^+$) substituents.

| | |
|---|---|
| monolinolein | 55.25% |
| acetylated monoglyceride | 9.75% |
| polymer | 35.00% |
| | (Eastman AQ 48 (35%)) |

Although the present invention has been described in terms of the presently preferred embodiment, it is to be understood that such disclosure is not to be interpreted as limiting to the invention described herein. No doubt that after reading the disclosure, various alterations and modifications will become apparent to those skilled in the art to which the invention pertains. It is intended that the appended claims be interpreted as covering all such alterations and modifications as fall within the spirit and scope of the invention.

We claim:

1. A composition comprising:
   A) about 55 to about 90 weight percent of a mixture of monoglycerides having an acyl chain of 12 to 22 carbons;
   B) about 5 to about 35 weight percent of a mixture of acetylated monoglycerides having an acyl chain of 12 to 22 carbons; and
   C) about 2 to about 40 weight percent water;
   wherein the total weight of said three components equals 100 weight percent.

2. The composition of claim 1 having a weight ratio of about 1:1 to about 4:1 of said monoglyceride to water.

3. The composition of claim 1 having a weight ratio greater than about 4:1 of said monoglyceride to water.

4. The composition of claim 1 wherein said composition is in a liquid crystalline phase and has a viscosity between about 10 to 25,000 cPs at a temperature between about 20 to about 8020 C.

5. The composition of claim 4 wherein said viscosity is about 100 to 15,000 cPs at a temperature between about 20 to 40° C.

6. The composition of claim 4 wherein said liquid crystalline phase is in a cubic liquid crystalline phase.

7. The composition of claim 6 wherein said cubic liquid crystalline phase composition is a gel.

8. The composition of claim 1 comprising about 65 to about 85 weight percent monoglyceride, about 10 to about 30 weight percent acetylated monoglyceride, and about 5 to about 25 weight percent water.

9. The composition of claim 1 wherein said monoglyceride and said acetylated monoglyceride have an unsaturated acyl chain.

10. The composition of claim 9 wherein said unsaturated acyl chains are selected from the group consisting of the esters of palmitic acid, stearic acid, oleic acid, linoleic acid, linolenic acid, gadoleic acid, behenic acid, and combinations thereof.

11. The composition of claim 10 wherein said monoglyceride component includes glyceryl monooleate, glyceryl monoleate, or a combination thereof.

12. The composition of claim 1 further comprising an active ingredient dispersed therein.

13. The composition of claim 12 wherein said active ingredient is selected from the group consisting of vitamins, proteins, peptides, nucleic acids, growth promoters, fragrances, sunscreens, antifungals, antibiotics, benzocaine, phenols, polymers, insecticides, steroids, antimicrobials, humectants, moisturizers, astringents, deodorants, and combinations thereof.

14. A process of making a liquid crystalline gel comprising: blending together, at a temperature between about 60 to about 90° C., about 55 to about 90 weight percent of a mixture of monoglycerides having an acyl chain of about 12 to about 22 carbons, about 5 to about 35 weight percent of a mixture of acetylated monoglycerides having an acyl chain of about 12 to about 22 carbons, and about 2 to about 40 weight percent water, wherein the total of said weight percentages equals 100 weight percent.

15. The process of claim 14 wherein said water is added to a molten blend of said monoglyceride and said acetylated monoglyceride.

16. The composition of claim 1 further comprising up to about 10 weight percent of a wax, with said weight percent being based on the total weight of said composition.

17. The composition of claim 2 wherein said composition has a lower viscosity and gel temperature relative to a binary composition having said weight ratio of said monoglyceride and water.

18. The composition of claim 3 wherein said composition has a higher viscosity and gel temperature relative to a binary composition having said weight ratio of said monoglyceride and water.

19. A method of using the composition of claim 18 comprising:
   a) applying said composition to a surface wherein said surface is at a temperature above a first gel temperature of said composition; and
   b) supplying an effective amount of water to said composition to shift said gel temperature to a second gel temperature.

20. The method of claim 19 wherein said second gel temperature is greater than said surface temperature.

21. The method of claim 20 wherein said second gel temperature is greater than said first gel temperature.

22. The method of claim 19 wherein said water is supplied by absorption from said surface.

23. The method of claim 22 wherein said surface skin, a mucosal membrane, or a bodily tissue.

24. The method of claim 19 wherein said composition comprises from about 2 to about 5 weight percent water.

25. A cubic liquid crystalline phase gel comprising:
   A) about 55 to about 90 weight percent of a mixture of monoglycerides having an acyl chain of 12 to 22 carbons;
   B) about 5 to about 35 weight percent of a mixture of acetylated monoglycerides having an acyl chain of 12 to 22 carbons; and
   C) about 2 to about 40 weight percent water;
wherein the total weight of said three components equals 100 weight percent.

26. The composition of claim 12 wherein the active ingredient is selected from the group consisting of hydrophobic compounds, hydrophilic compounds, amphiphilic compounds, pharmaceutical agents, and combinations thereof.

27. The composition of claim 26 wherein the active ingredient is a pharmaceutical agent.

* * * * *

UNITED STATES PATENT AND TRADEMARK OFFICE
CERTIFICATE OF CORRECTION

PATENT NO. : 6,235,312 B1
DATED : May 22, 2001
INVENTOR(S) : Hobbs et al.

It is certified that error appears in the above-identified patent and that said Letters Patent is hereby corrected as shown below:

Column 16, claim 4,
Line 14, "8020 C" should be -- 80°C --.

Signed and Sealed this

Sixteenth Day of October, 2001

Attest:

*Nicholas P. Godici*

NICHOLAS P. GODICI
*Attesting Officer*    *Acting Director of the United States Patent and Trademark Office*